United States Patent [19]
Guibor

[11] 3,948,272
[45] Apr. 6, 1976

[54] RECONSTRUCTION DEVICE FOR LACRIMAL DRAINAGE DUCTS

[75] Inventor: Pierre Guibor, New York, N.Y.

[73] Assignee: Procedure Medical Products, Inc., New York, N.Y.

[22] Filed: Apr. 8, 1975

[21] Appl. No.: 566,622

[52] U.S. Cl. .................................. 128/350 R; 3/1
[51] Int. Cl.² A61M 27/00; A61M 25/00; A61F 1/24
[58] Field of Search.......... 3/1; 128/348, 1 R, 351 R, 128/DIG. 21

[56] References Cited
UNITED STATES PATENTS
2,154,968   4/1939   Alkio ................................. 128/348
3,726,284   4/1973   Parker ............................ 128/350 R Primary Examiner—Ronald L. Frinks
Attorney, Agent, or Firm—Silverman and Jackson

[57] ABSTRACT

The present invention constitutes a reconstructive replacement channel for the lacrimal drainage ducts. It includes a pair of stainless steel probes as well as a length of silicone tubing which is left in vivo after completion of an operation. The two probes, each of which are surrounded by lengths of silicone tubing, are fed into the lacrimal sac, through the tear ducts, and finally into the upper cavity of the nose. Each probe is fed inward to the lacrimal sac which exists between the inner corner of the eye and the upper bridge of the nose. The probe is produced in the shape of a helix in order to enable it to be fed with greater ease into the lacrimal passageway.

5 Claims, 5 Drawing Figures

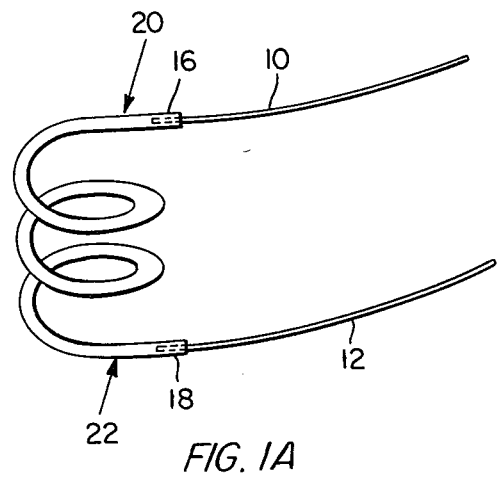
FIG. IA
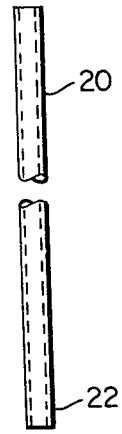
FIG. 2
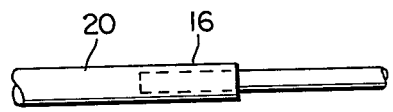
FIG. IB
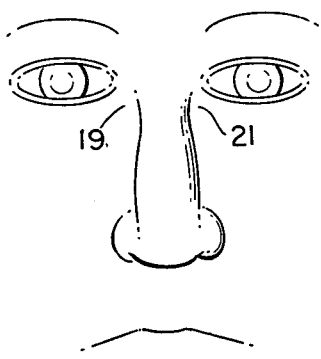
FIG. 4
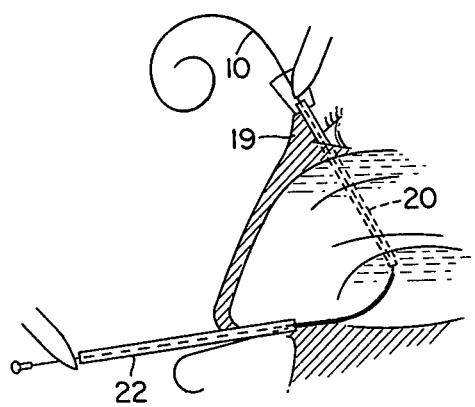
FIG. 3

RECONSTRUCTION DEVICE FOR LACRIMAL DRAINAGE DUCTS

BACKGROUND OF THE INVENTION

The present invention relates to a replacement tube for the lacrimal drainage ducts and, more particularly, to a replacement tube which, when implanted within the tear duct of a patient, will not subsequently become dislodged or rejected.

Lacrimal fluid or tears are continuously supplied from the lacrimal gland, located laterally and superiorly of the eye, through the upper lacrimal duct, and to the conjunctival sac in which the eyeball is partially encased. Hence, the lacrimal fluid washes across the sclera and other conjunctival components, and also the cornea. Under normal conditions, excess lacrimal fluid beyond that which is retained by the eye and conjunctiva is drained from the inner canthus to the nasal passages and to the inferior nasal meatus in particular. The flow of lacrimal fluid, under normal conditions, is continuous but in varying amounts. In normal function, any excessive lacrimal fluid will brim over the eyelids in the form of tears. At other times, the excess fluid is drained through a network of passageways commencing with the puncta which appear as a small papilla adjacent the inner canthus or inner corner of the eye. Therefore, the lacrimal fluid is collected in the lacrimal sac by a number of canaliculi connecting the puncta with the lacrimal sac. The canaliculi run inferiorly then medially to the lacrimal sac. The lacrimal sac is drained through its extension, the nasolacrimal duct which passes into the inferior nasal meatus for this purpose. This network of passages is referred to herein and in the claims as the lacrimal drainage ducts.

Quite often a permanent closure occurs in the canaliculi, the lacrimal sac, or the nasolacrimal duct, whereupon the lacrimal fluid no longer can be disposed of in the normal manner. Such closure or stenosis can result from congenital anomalies, accident, inflammation or other disease, as well as advancing age. In addition, the canaliculi may become scarred from conjunctival infection. Epiphora likewise can result from blockage of the canaliculi by a cilium or by streptothrix concretions. In severe cases permanent stenosis occurs and a dacryocystorhinostomy is indicated.

Upon occurrence of blockage in the lacrimal drainage ducts, the eye, of course, is continuously brimming over with tears much to the discomfort, annoyance, and embarrassment of the individual so affected. A much more serious consequence is the potential for stagnating tears that may result in infection and inflammatory irritation of the mucous membrane with proliferation of the epithelium, hyperemia, and a purulent exudation into the conjunctiva.

In some cases the defective portion of the lacrimal drainage system can be reconstructed by surgery, as when performing a dacryocystorhinostomy. If blockage occurs in the nasolacrimal duct, for example, the latter can be removed, and the lacrimal sac cavity can be joined directly with the nasal fossa (mucosa) after removing a segment of the nasal bone and periosteum to restore drainage of the tears in a more or less natural manner. In most cases, however, removal of the entire lacrimal drainage system and replacement thereof with a mechanical contrivance or replacement tube, by dacryocystorhinostomy, is indicated. Although such operations are frequently performed, they are seldom entirely successful. At least two prominent difficulties have been almost uniformly experienced with such operations in the past. In the first instance, although the nasal bone apparently heals about the lower end portion of the replacement tube, the replacement tube gradually is rejected from the bone and flesh of the patient. Secondly, the patient's flesh heals over the upper end of the replacement tube at the inner canthus and must be reopened periodically.

One approach to the solution of the above described problems appears in the patent to Alkio, U.S. Pat. No. 2,154,968 (1939). Said patent discloses a method of enlarging and draining the lacrimal duct. This method comprises the inserting of a tube in said duct in order to preliminarily enlarge the same, thereafter inserting a spiral cannula into said duct, through the nose and behind the tube. The tube and the cannula are then drawn upwardly in the duct. The tube is then removed with the cannula remaining in the duct for drainage of secretions between the spirals of the cannula. In essence, the method of Alkio comprises the use of thin metal wire formed in spiral shape which is utilized as a support and drainage means for a damaged lacrimal duct.

A patent to Parker, U.S. Pat. No. 3,726,284 (1973) discloses a replacement tube for the lacrimal drainage ducts which tube includes a pair of elongated end portions. The replacement tube includes an expanded central portion having a drainage passage which adjoins adjacent ends of the end portions. Each of said end portions exhibits a drain passage extending therethrough and communicating with the expanded portion. Said portion forms relatively abrupt junctions at generally opposite sides thereof in order to prevent rejection of the replacement tube.

Other art of this general category appears in Class 128, Sub-Class 350.

SUMMARY OF THE INVENTION

An object of the present invention is to provide an improved means for reconstructing lacerated canalicula, such as may result from accident.

Another object is to provide a means for reconstructing canaliculi in those cases involving dacrocystorhynostomy with obstruction of the common canaliculus.

A further object is to provide a replacement tube for lacrimal drainage ducts in children suffering from a lacrimal obstruction.

The above and other objects are obtained through the use of two specially arched and configured stainless steel probes bonded to an intermediary length of silicone tubing.

BRIEF DESCRIPTION OF THE DRAWINGS

FIG. 1a is a schematic perspective view of the present device prior to insertion into a patient.

FIG. 1b is an enlarged view of the interconnection between the end of one probe and the beginning of the silicone tubing.

FIG. 2 is a breakaway schematic view of a length of the silicone tubing herein utilized.

FIG. 3 is a cross-sectional schematic view showing an insertion of the present canaliculus device into the lacrimal ducts of the patient.

FIG. 4 is a perspective view of the facial area of a patient affected by the present method.

DETAILED DESCRIPTION OF THE INVENTION

Shown in FIG. 1a is a first and a second specially arched stainless steel probe 10 and 12, respectively. It is to be noted that each probe 10 and 12 is provided with a slight arch which may vary between ten and thirty degrees from one end with respect to the other. The probes 10 and 12 are bonded to the tubing 20, 22 at points 16 and 18 respectively.

The purpose of the arched probes is to facilitate insertion of silicone tubing 20, 22 into a lacrimal duct (see FIG. 3). More particularly, each probe serves to properly position the silicone tubing within the upper drainage system of the eye, that is, within the lacrimal ducts. These ducts originate within a structure termed the lacrimal sac, and then travel downwardly until reaching their final termination in the upper cavity of the nose.

The insertion of the silicone tubing is achieved through the following procedure:

1. The upper and lower puncta, which comprise the hollow regions on the left and right sides of the bridge of the nose, are fully dilated. These areas are indicated as elements 19 and 21 in FIG. 4.

2. The nose is then fully packed with adrenalin strips.

3. An illuminated nasal speculum is utilized in order to obtain direct visualization of the probe tip 12.

4. The physician grasps only the tip of the probe as it enters one nostril of the nose and then gently directs it upward to the lacrimal duct. See FIG. 3.

5. During insertion the probe is guided in an arc and ultimately grasped upon exit from the inner corner of the eye with a Kelly clamp.

6. Following inturbation, a silk or nylon 4.0 or 5.0 suture is placed around the two extremities of the nose.

7. Sutures are left in place for a period of time which varies in accordance with the type of operation; that is, in the case of a dacrocystorhynostomy, the sutures are left in for two weeks. In the case of a lacerated canaliculus, the sutures are retained for a period of between 2 and 6 months. In the case of an infectious obstruction of the canaliculus, they are left in for six months.

In order to remove the excess length of tubing, it is cut at the medial conthus. The conthus comprises that angle at either end of the slit between the eyelids. The unneeded length of tubing is pulled out of the nose with a forceps.

Where one is unable to grasp the nasal ends of the tubes, neo-synephrine 10% nasal drops or spray are utilized. In the alternative, it is sometimes possible for the patient to expel the excess parts of tubing by blowing his nose.

The configuration of the probe itself comprises a length of stainless steel approximately 7 inches in length and provided with either an arch, as illustrated in FIG. 1, or a tightly wound helix. The purpose of the helix design is to enable the probe to be fed into the lacrimal passageway with greater ease.

The length of the tubing 20, 22 that is implanted within the lacrimal duct is about 12 inches long.

It has been found that the use of silicone tubing is particularly compatible for implant procedures of this nature.

It is thus seen that the object of obtaining an improved Canaliculus Intubation device has been efficiently attained by the above-described embodiments of the present invention.

While there have been herein shown and described the preferred embodiments of the present invention, it will be understood that the invention may be embodied otherwise than as herein specifically illustrated or described and that within said embodiments certain changes in the detail and construction, and the form of arrangement of the parts may be made without departing from the underlying idea of principles of this invention within the scope of the appended claims.

Having thus described my invention what I claim as new, useful and non-obvious and accordingly secure by Letters Patent of the United States is:

1. A reconstruction device for the lacrimal drainage ducts comprising:
    a pair of arched probe members, each arch being between ten and thirty degrees; and
    a length of tubing affixed at the ends thereof to one of each ends of said arched probes,
    whereby said arched probe members serve to facilitate the insertion of said tubing into and through the lacrimal ducts during the performance of reconstructive surgery.

2. The device as recited in claim 1 in which said probes comprise stainless steel.

3. The device as recited in claim 1 in which said tubing is formed of silicone.

4. The device as recited in claim 1 in which said tubing is circumferentially affixed about the ends of said arched probes.

5. The device as recited in claim 1 in which said tubing is abuttingly affixed to the ends of said arched probes.

* * * * *